United States Patent [19]

Gould et al.

[11] Patent Number: 4,624,657

[45] Date of Patent: Nov. 25, 1986

[54] MEDICAL DEVICES HAVING INFLATABLE PORTIONS

[75] Inventors: Arnold S. Gould, Bedford; Michael A. Ciannella, Marlboro, both of Mass.

[73] Assignee: Medi-Tech, Incorporated, Watertown, Mass.

[21] Appl. No.: 551,861

[22] Filed: Nov. 15, 1983

[51] Int. Cl.⁴ .......................................... A61M 29/00
[52] U.S. Cl. ..................................... 604/103; 604/96
[58] Field of Search .................. 128/344; 604/96, 103, 604/266

[56] References Cited

U.S. PATENT DOCUMENTS

| | | |
|---|---|---|
| 3,192,949 | 7/1965 | DeSee . |
| 3,434,869 | 3/1969 | Davidson ............................ 604/266 |
| 3,467,101 | 9/1969 | Fogarty et al. . |
| 3,889,685 | 6/1975 | Miller, Jr. et al. .................. 128/344 |
| 3,924,634 | 12/1975 | Taylor et al. . |
| 3,983,879 | 10/1976 | Todd . |
| 4,222,384 | 9/1980 | Birtwell . |
| 4,254,774 | 3/1981 | Boretos . |
| 4,265,848 | 5/1981 | Rusch . |
| 4,350,161 | 9/1982 | Davis, Jr. . |

Primary Examiner—C. Fred Rosenbaum
Assistant Examiner—Gene B. Kartchner

[57] ABSTRACT

A medical device includes a flexible, elongated tube having a continuous, smooth, outer surface, adapted for introduction into the body, and a connection for introducing inflation fluid into the space defined by the length of the tube. The tube is elastomer and the tube wall is in a weakened state while adjacent portions of the tube are not so weakened, the wall of the selected portion having a lower resistance to expansion than adjacent portions. By use of heat-sensitive, annealable plastic, a tube of uniform thickness is weakened at a selected location by annealing. The selected limited-length portion, by reason of its weakened state, is adapted to preferentially respond to pressure of inflation fluid within the tube by expanding transversely to a balloon shape larger than adjacent portions of the tube that are subjected to the same pressure. In a preferred embodiment, the device includes a tube surrounded by a sleeve having the limited-length, preferentially expansive portion and anti-stick means in the preferred form of a porous inner sleeve extends between the outer sleeve and the central member. The outer sleeve extends about the end of the central member to define the lead surface.

12 Claims, 7 Drawing Figures

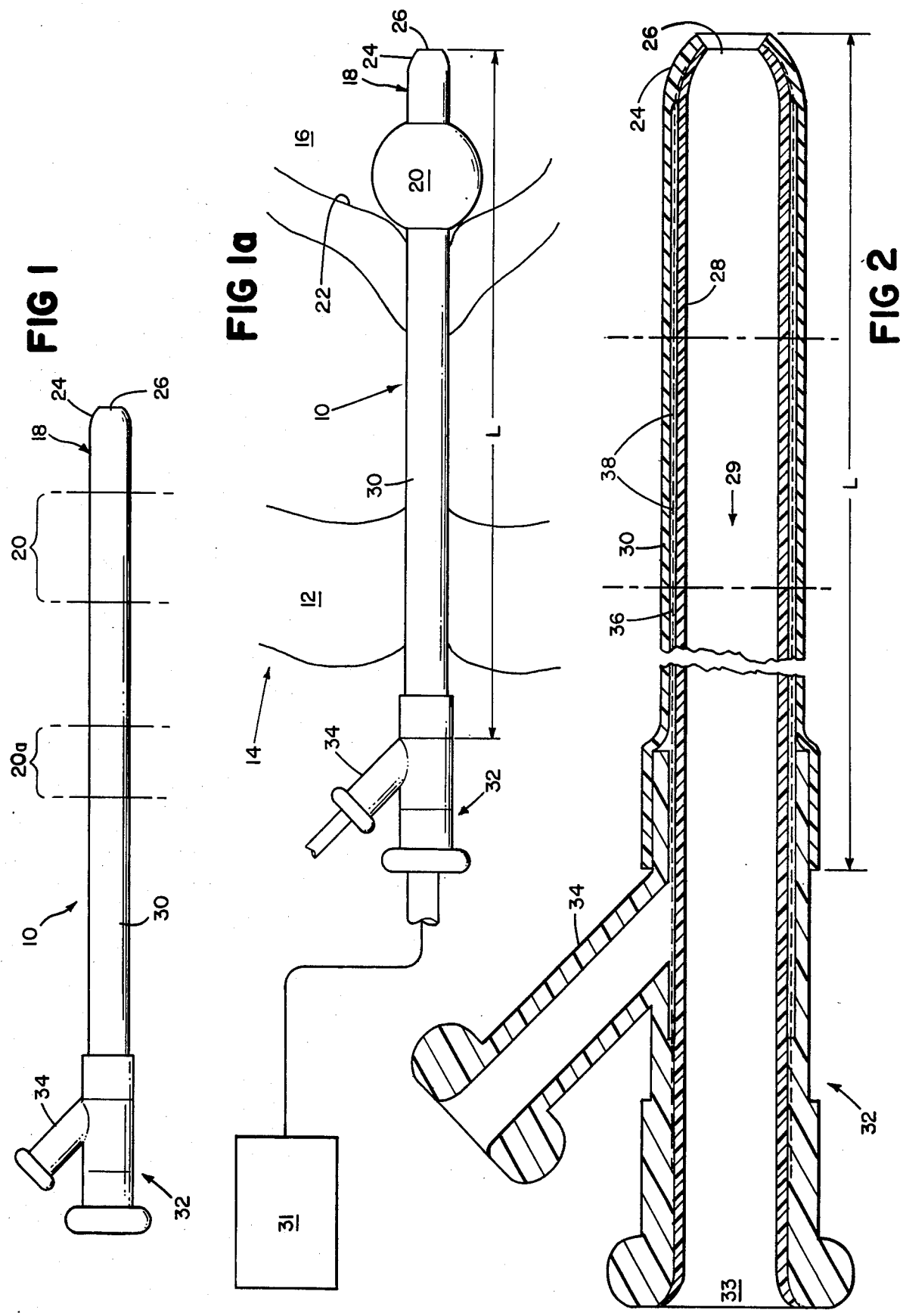

MEDICAL DEVICES HAVING INFLATABLE PORTIONS

BACKGROUND OF THE INVENTION

The invention relates to catheters, and other medical devices for introduction into the body, which have inflatable portions.

Such devices have many functions in medical treatment. For example, coaxial or multi-lumen catheters are inserted and anchored in position by a balloon expanded within an organ to provide a fixed conduit for delivering or draining fluids. Examples are shown in Todd U.S. Pat. No. 3,983,879; Rusch U.S. Pat. No. 4,265,848 and ,Davis, Jr. U.S. Pat. No. 4,350,161. Single lumen, occlusion-type catheters are inserted into a flow path of the body, typically into arteries or veins during surgery, and a ballooned portion is used to block blood flow to an operating site. An example of this type catheter is shown in Fogerty et al. U.S. Pat. No. 3,467,101.

The ballooning portion of a typical catheter design is formed separately and is attached over the main catheter body, with a typical surface discontinuity or lateral protrusion at the point of attachment. These discontinuities can cause trauma to the tissue surrounding the point of insertion, and can hinder the insertion procedure. Other ballooning portions are formed by folding the balloon into the catheter, e.g. see Boretos U.S. Pat. No. 4,254,774, or by thinning the catheter wall, e.g. see De See U.S. Pat. No. 3,192,949, which involve difficulties in manufacture as well as in use.

SUMMARY OF THE INVENTION

According to the invention, a medical device comprises a flexible, elongated tubular member of substantially uniform thickness having a continuous, smooth outer surface, adapted for introduction into the body, the tubular member is comprised of heat-sensitive elastomer and, as formed, has a predetermined resistance to expansion. A selected, limited-length tubular portion of the wall of the tubular member is in a post-formation annealed state while adjacent tubular portions are not so annealed, the wall of the selected tubular portion having a lower resistance to expansion than adjacent portions. A connection is provided for introducing inflation fluid into the space defined by the length of the tubular member, the selected limited-length portion, by reason of the annealed state, being adapted to preferentially respond to pressure of inflation fluid within the tubular member by expanding transversely to a balloon shape larger than adjacent portions of the tubular member that are subjected to the same pressure. The distal end of the tubular member can smoothly reduce in size with no lateral protrusion, and the tubular member can extend proximally therefrom for as long a distance as desired, e.g. for more than a majority of the length, to a point on the catheter which does not enter the body.

In preferred embodiments of the invention, the heat-sensitive elastomeric substance is annealable polyurethane having durometer of about 80A and the substance has characteristic elongation of at least 400% or more.

According to another aspect of the invention, a central member is provided within an elongated, exterior tubular sleeve, as described above. Preferably a low-sticking substance is provided between the corresponding surfaces of exterior and interior members, preferably this being provided as a separate, inner, porous sleeve, e.g. of fluorocarbon fibers. In this case, the distal point of attachment of the sleeve to the central member can occur at a reduced-diameter region, preferably an end portion of the sleeve defining the end surface of the device, covering the end of the central member. (This construction, broadly, can also be of use where means other than annealing are used to provide the preselected weakened region of the central member.)2

In one preferred embodiment, the means for introducing an inflation fluid between sleeve and central member is via an aperture defined through the wall of the central member at a point underlying the sleeve.

PREFERRED EMBODIMENT

We first briefly describe the drawings.

DRAWINGS

FIG. 1 is a side view of a coaxial balloon catheter, constructed according to the invention, in uninflated state, while FIG. 1a is a side view of the catheter of FIG. 1 lodged by percutaneous entry through the wall of a patient's stomach;

FIG. 2 is a side section view of the catheter shown in FIG. 1;

Figure 3:
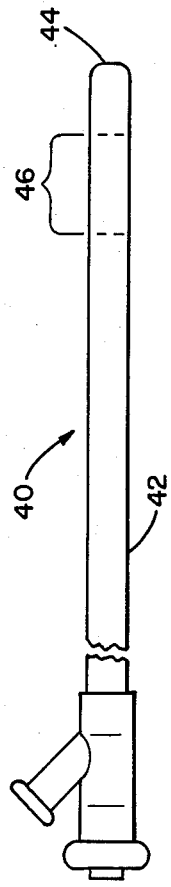
FIG. 3 is a side section view of a closed-ended device constructed according to the invention.

Referring to FIG. 1, a coaxial-lumen balloon catheter 10 is shown with a smooth, constant diameter, protrusion-free outer surface in uninflated state, to facilitate percutaneous insertion through a patient's tissue. In FIG. 1a, the same catheter is shown inserted through the abdomen wall 12 of a patient 14 into the stomach 16. Adjacent the distal end 18 of catheter 10, the portion 20 of the outer sheath, locally annealed according to the invention, has been expanded preferentially to an enlarged balloon state to prevent dislodgement, and rests against the inner surface 22 of the stomach.

Referring also to FIG. 2, at the distal tip 24, aperture 26 opens from the central lumen 28 of catheter 10, which forms a conduit 29 for introduction of nourishment to the stomach from outside source 31. Central lumen or tubing 28 is enclosed substantially over its length and at its distal end 24 by sleeve 30. At the narrowed distal tip, the overlying, narrowed terminal portion of sleeve 30 is bonded to a corresponding terminal portion of central tube 28. At the proximal end 32, sleeve 30 is sealed to inflation connection 34 which in turn is sealed to central tubing 28 to form annular space 36, primarily between sleeve 30 and tubing 28. Inflation connection 34 is provided to allow introduction, typically by syringe, of inflation fluid, e.g. saline or sterile water, into annular space 36 to increase the pressure therewithin to inflate enlarged balloon 20 at the desired position as discussed more fully below. An anti-stick (low adherence) substance is provided to prevent adhesion between sleeve and central tubing, herein comprising an inner sleeve 38, e.g. 0.003 inch fluorocarbon polymer fibers (e.g. DuPont's Teflon) woven to form a 0.006 inch thick mesh, which has the added advantage of defining fluid passages of non-wettable substance to ensure proper flow of inflation fluid to balloon 20. Central tubing 28 is a 0.130 inch outer diameter (10 French) tube of semi-rigid polyurethane having hardness of about 70D and wall thickness of 0.015 inch. At the proximal end 32, the conduit-forming lumen 29 is open at 33 to receive fluid.

The external sleeve 30 is a 0.169 inch outer diameter (13 French) tube of elastomeric material having high elongation characteristics, typically 0.010 inch wall thickness polyurethane of 80A durometer capable of elongation of at least 400%, preferably up to about 800%. The external surface of the sleeve is smooth, with no potentially-trauma-inducing irregularities. The sleeve 30 is sealed to the wall of the central tubing 28 at the distal end 18, forming a tip 24 of narrowed diameter, relative to the general diameter of the catheter, with the material of the sleeve extending to the distal end surface of the catheter. Thus a smooth end is provided to facilitate insertion of the catheter into the patient's body. The fiber mesh 38 prevents the fluid passage space 36 from closing due to adhesion of the sleeve to the wall during sterilization or, more critically, after an extended period of use when the space 36 is evacuated to deflate the balloon for removal from the patient.

Adjacent the distal end 18, over a limited portion 20 of its length, sleeve 30 is treated by controlled heating to anneal the elastomeric material and thus weaken the material (as by elimination of strength-imparting molecular orientation that may result from stretching during manufacture). This annealing process, e.g., for the materials described, immersion for 30 seconds in water at 165° F., has been found satisfactory to locally reduce the resistance of the sleeve wall to transverse expansion under pressure. When the annealing is performed after assembly, the fluorocarbon sleeve again can prevent unwanted adhesion between the outer tube and the inner structure.

When inflation fluid, e.g. 3 to 5 cc. from a syringe, is introduced via connection 34 into the annular space 36 to increase the pressure therewithin, the annealed portion of the sleeve will, as desired, expand preferentially relative to adjacent portions of the same thickness but unannealed sleeve material, thus forming the desired balloon.

Figure 3A:
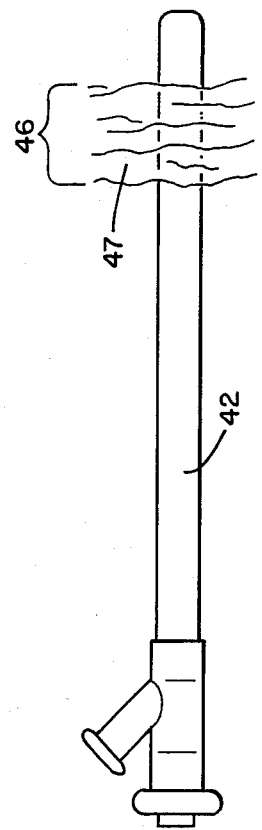
FIGS. 3a and 3b are similar views of the device of FIG. 3, shown during annealing and after inflation, respectively.
Figure 3B:
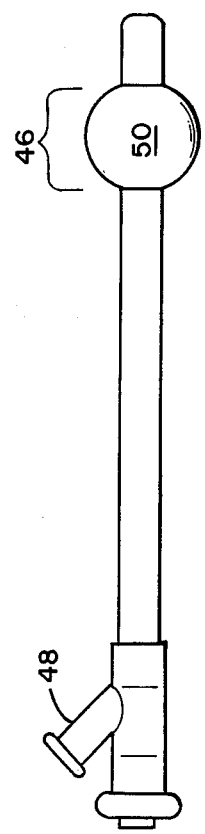

In FIGS. 3, 3a and 3b, an occlusion-type catheter 40 is shown. It is comprised of a singled-walled tube 42 with a closed tip 44. Tube 42 has material characteristics similar to those of external sleeve 30 in FIGS. 1, 1a and 2, i.e. it is an elastomeric material having high elongation. Referring to FIG. 3a, a selected, limited portion 46 of the length of tube 42 is annealed by immersion in water 47 at about 165° F. for 30 seconds. When treatment is complete, the catheter is allowed to return to room temperature. In use, the catheter 40 is inserted into the patient's body, typically by means of a rigid introducer extending to the catheter tip. After the catheter is inserted and the introducer removed (FIG. 3b), the catheter 40 is connected to a source of inflation fluid via connection 48. Responsive to increase in pressure, catheter 40 preferentially expands transversely in the area of treatment 46 to form balloon 50, e.g. to occlude the flow passage in which it is lodged. (The increased pressure may also cause some slight expansion over the length of tube 42, which may have the desirable effect of further sealing the passage against fluid leaks along path of insertion.)

OTHER EMBODIMENTS

Figure 4:
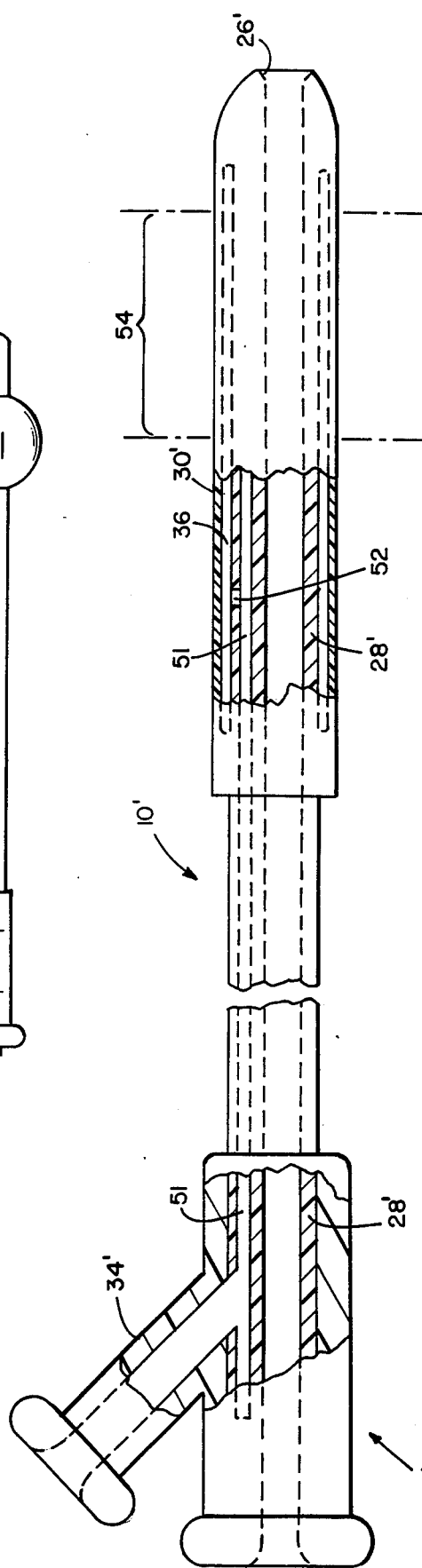
FIG. 4 is a side section view of the distal portion of still another embodiment of the invention.

Other embodiments of the invention are within the following claims. For example, in FIG. 4, sleeve 30' is sealed to the wall of a double-lumen catheter 10' distal of the proximal end 32' of the catheter. In this embodiment, a first lumen 28' extends through the catheter to define a conduit between distal opening 26' and the proximal end 32'. Inflation fluid is introduced via connection 34' into the inner volume of a second, typically smaller lumen 51 and is transmitted to the space 36' between the sleeve and the wall of the catheter 10' via aperture 52 to inflate treated portion 54. The catheter may be selectively treated at any point along the length, or may be treated at multiple points, e.g. 20a, FIG. 1. Also, where a treated sleeve is employed, the central tubing may be a rigid material, e.g. steel.

We claim:
1. A medical device comprising
   a flexible, elongated, tubular member of uniform wall thickness having a continuous, smooth outer surface of uniform outer diameter, adapted for introduction into the body,
   said tubular member comprised of heat-sensitive elastomer, said tubular member, as formed, having a predetermined resistance to expansion,
   a selected, limited-length tubular portion of the wall of said tubular member being in a post-formation, annealed, weakened state while adjacent portions of said tubular member are not so annealed, the wall of said selected portion having a lower resistance to expansion than said adjacent portions of said wall having uniform thickness, and
   a connection for introducing inflation fluid into the space defined by the length of said tubular member,
   said selected limited-length portion by reason of said annealed state, adapted to preferentially respond to pressure of inflation fluid within said tubular member by expanding transversely to a balloon shape larger than said adjacent portions of said tubular member that are subjected to the same pressure.
2. A medical device comprising
   an elongated central member, and
   means adapted to define an inflatable balloon over a desired length about the exterior of said central member,
   said means comprising an elongated, exterior, elastomeric sleeve of uniform wall thickness having a continuous, smooth, outer surface of uniform outer diameter, adapted for introduction into the body, said sleeve extending about said central member along a length substantially exceeding the desired length of said balloon, the ends of said sleeve being sealed to form a closed space with said central member, the distal point of seal being of reduced diameter relative to the main body of said central member,
   said sleeve comprised of heat-sensitive elastomer having a predetermined resistance to expansion,
   a selected, limited-length, tubular portion of the wall of said sleeve being in a post-formation annealed state while adjacent portions of said tubular member are not so annealed, the wall of said selected portion having a lower resistance to expansion than said adjacent portions of said wall, said selected portion and said adjacent portions of said wall having uniform thickness,
   a connection for introducing an inflation fluid into the space defined between the length of said sleeve and said central member, said sleeve in the uninflated state closely surrounding said member, and
   means disposed at the interface between opposed walls of said sleeve and said member to facilitate transmission of pressure via said fluid within said sleeve between said connection and adjacent the selected portion of said wall, said selected limited-length portion of said sleeve, by reason of said annealed state, adapted to preferentially respond to pressure of inflation fluid within said space by expanding transversely to a balloon shape larger than said adjacent portions of said tubular member that are subjected to the same pressure.

3. The device of claim 2 wherein the distal end surface of said device is defined by a portion of said sleeve overlying the terminal portion of said central member.

4. The medical device of claim 2 or 3 wherein said means at said interface comprises material having low adherance to said opposed surfaces.

5. The medical device of claim 4 wherein said means comprises a porous inner sleeve.

6. The medical device of claim 5 wherein said substance is fluorocarbon.

7. A medical device comprising an elongated, exterior, elastomeric sleeve of uniform wall thickness having a continuous, smooth, outer surface of uniform outer diameter, adapted for introduction into the body, said sleeve extending about said central member along a length substantially exceeding the desired length of said balloon, the ends of said sleeve being sealed to form a closed space with said central member, the distal point of seal being of reduced diameter relative to the main body of said central member, the distal end surface of said device being defined by a portion of said sleeve overlying the terminal portion of said central member, said sleeve comprised of elastomer having a predetermined resistance to expansion, a selected, limited-length, tubular portion of the wall of said sleeve being in a weakened state while adjacent portions of said tubular member are not so weakened, the wall of said selected portion having a lower resistance to expansion than said adjacent portions of said wall, said selected portion and said adjacent portions of said wall having uniform thickness, a connection for introducing an inflation fluid into the space defined between the length of said sleeve and said central member, said sleeve in the uninflated state closely surrounding said member, and means disposed at the interface between opposed walls of said sleeve and said member to facilitate transmission of pressure via said fluid within said sleeve between said connection and adjacent the selected portion of said wall, said means comprising material having low adherence to said opposed walls, said selected limited-length portion of said sleeve, by reason of said weakened state, adapted to preferentially respond to pressure of inflation fluid within said space by expanding transversely to a balloon shape larger than said adjacent portions of said tubular member that are subjected to the same pressure.

8. The medical device of claim 1, 2 or 7 wherein said elastomer is polyurethane having durometer of about 80A.

9. The medical device of claim 1, 2 or 7 wherein said elastomer has characteristic elongation of about 400% or more.

10. The medical device of claim 2, 3 or 7 wherein said external sleeve extends for a majority of the length of said central member.

11. The medical device of claim 2, 3 or 7 wherein said means for introducing an inflation fluid into said space communicates with said space via an aperture defined through the wall of said central member at a point underlying said sleeve.

12. The medical device of claim 9 wherein said elastomer is substantially elastic.

* * * * *